(12) United States Patent
Kharidehal et al.

(10) Patent No.: US 11,694,289 B2
(45) Date of Patent: Jul. 4, 2023

(54) SYSTEM AND METHOD FOR CONVERSION ACHIEVEMENT

(71) Applicant: CERNER INNOVATION, INC., Kansas City, KS (US)

(72) Inventors: Arun Kharidehal, Bangalore (IN); Jaipal Reddy, Bangalore (IN); Chaitanya S, Bangalore (IN); Darshan Shashidhara, Bangalore (IN); Deepak Gupta, Bangalore (IN); Pratyush Kumar, Bangalore (IN); Sandeep Aithal, Bangalore (IN)

(73) Assignee: Cerner Innovation, Inc., Kansas City, MO (US)

( * ) Notice: Subject to any disclaimer, the term of this patent is extended or adjusted under 35 U.S.C. 154(b) by 199 days.

(21) Appl. No.: 16/916,276

(22) Filed: Jun. 30, 2020

(65) Prior Publication Data
US 2021/0406095 A1 Dec. 30, 2021

(51) Int. Cl.
*G06Q 50/20* (2012.01)
*G06Q 10/0631* (2023.01)
*G06F 9/54* (2006.01)
*G16H 10/60* (2018.01)

(52) U.S. Cl.
CPC .......... *G06Q 50/205* (2013.01); *G06F 9/542* (2013.01); *G06Q 10/0631* (2013.01); *G16H 10/60* (2018.01)

(58) Field of Classification Search
CPC .. G06Q 50/205; G06Q 10/0631; G06F 9/542; G16H 40/67
See application file for complete search history.

(56) References Cited

U.S. PATENT DOCUMENTS

| | | | |
|---|---|---|---|
| 8,135,612 B1 | 3/2012 | Scudder | |
| 10,326,748 B1 | 6/2019 | Brisebois et al. | |
| 10,417,613 B1* | 9/2019 | Brisebois | G06Q 10/1095 |
| 2002/0123983 A1* | 9/2002 | Riley | G06Q 10/00 |
| 2003/0046308 A1 | 3/2003 | Weber et al. | |
| 2005/0042593 A1 | 2/2005 | Hopkins et al. | |
| 2006/0059253 A1* | 3/2006 | Goodman | G06Q 10/10 709/223 |
| 2006/0161879 A1* | 7/2006 | Lubrecht | G06Q 10/06 717/101 |
| 2008/0126110 A1* | 5/2008 | Haeberle | G06F 9/542 717/168 |
| 2008/0162688 A1* | 7/2008 | Reumann | G06Q 30/02 709/224 |
| 2009/0043669 A1* | 2/2009 | Hibbets | G06Q 30/06 705/26.1 |
| 2009/0043882 A1* | 2/2009 | Hibbets | G06Q 10/10 709/224 |

(Continued)

OTHER PUBLICATIONS

Non-Final Office Action received for U.S. Appl. No. 17/138,003, dated Jun. 14, 2022, 14 pages.

(Continued)

*Primary Examiner* — Jimmy H Tran
(74) *Attorney, Agent, or Firm* — Invoke

(57) ABSTRACT

Methods, systems and computer storage media are disclosed for providing resources to a platform issue. Embodiments describe associating educational resources and an event resource to resolve the platform issue.

20 Claims, 12 Drawing Sheets

(56) References Cited

U.S. PATENT DOCUMENTS

| | | | |
|---|---|---|---|
| 2009/0063387 A1* | 3/2009 | Beaty | G06N 5/04 706/50 |
| 2009/0276728 A1 | 11/2009 | Doan et al. | |
| 2012/0066142 A1* | 3/2012 | Jenkins | G06Q 30/02 707/769 |
| 2012/0215560 A1 | 8/2012 | Ofek et al. | |
| 2012/0316962 A1 | 12/2012 | Rathod | |
| 2013/0171594 A1 | 7/2013 | Gorman et al. | |
| 2014/0006383 A1* | 1/2014 | Hacigumus | G06F 16/24539 707/718 |
| 2014/0149185 A1* | 5/2014 | Mukherjee | G06Q 10/0637 705/7.36 |
| 2014/0308646 A1 | 10/2014 | Wurth | |
| 2014/0310198 A1* | 10/2014 | Wamberg | G06Q 10/10 705/345 |
| 2014/0324552 A1* | 10/2014 | Chang | G06Q 10/06395 705/7.39 |
| 2016/0004820 A1 | 1/2016 | Moore | |
| 2016/0104067 A1 | 4/2016 | Xu et al. | |
| 2016/0147954 A1* | 5/2016 | Ng Tari | G16H 40/20 705/3 |
| 2016/0248698 A1 | 8/2016 | Sahu et al. | |
| 2017/0005967 A1* | 1/2017 | Simpson | G06Q 10/101 |
| 2017/0011308 A1 | 1/2017 | Sun et al. | |
| 2017/0054760 A1* | 2/2017 | Barton | G06F 21/54 |
| 2017/0126484 A1 | 5/2017 | Brew et al. | |
| 2018/0218305 A1* | 8/2018 | Shah | G06F 21/44 |
| 2018/0247648 A1* | 8/2018 | Nadimpalli | G10L 15/22 |
| 2018/0253487 A1* | 9/2018 | Carteri | G06Q 30/016 |
| 2018/0260760 A1* | 9/2018 | Srivastava | G06Q 10/06313 |
| 2018/0285750 A1 | 10/2018 | Purushothaman et al. | |
| 2019/0138964 A1* | 5/2019 | Morita | G06Q 10/06315 |
| 2019/0318295 A1* | 10/2019 | Srivastava | G06Q 10/063118 |
| 2019/0325323 A1* | 10/2019 | Walthers | H04L 41/5061 |
| 2019/0347668 A1* | 11/2019 | Williams | H04L 51/02 |
| 2020/0012548 A1* | 1/2020 | Escutia Garcia | G06F 11/3409 |
| 2020/0013070 A1 | 1/2020 | Walthers et al. | |
| 2020/0065342 A1* | 2/2020 | Panuganty | G06F 16/24578 |
| 2020/0089813 A1* | 3/2020 | Chauhan | H04L 67/535 |
| 2020/0151648 A1 | 5/2020 | Gorny | |
| 2020/0226481 A1 | 7/2020 | Sim et al. | |
| 2020/0244605 A1* | 7/2020 | Nagaraja | G16H 40/67 |
| 2020/0335183 A1 | 10/2020 | Tommasi et al. | |
| 2020/0410450 A1 | 12/2020 | Malhotra et al. | |
| 2021/0064642 A1* | 3/2021 | Qian | G06F 16/90332 |
| 2021/0074437 A1* | 3/2021 | Zeiger | G16H 80/00 |
| 2021/0081819 A1 | 3/2021 | Polleri et al. | |
| 2021/0109918 A1 | 4/2021 | Botea et al. | |
| 2021/0271362 A1 | 9/2021 | Rydzewski et al. | |
| 2022/0159124 A1 | 5/2022 | Gorny et al. | |
| 2022/0391270 A1 | 12/2022 | Gnanasambandam et al. | |

OTHER PUBLICATIONS

Non-Final Office Action received for U.S. Appl. No. 17/138,010, dated Jul. 21, 2022, 13 pages.

Non-Final Office Action received for U.S. Appl. No. 17/137,998, dated Aug. 4, 2022, 13 pages.

* cited by examiner

MEDICAL CENTER:1-3H7XXBV:_CA HNA 2016 ISSUES | TIMEZONE:PACIFIC TIME (US & CANADA)

⊕ ADD ISSUE                                                                                              HANDOFF

ISSUES                         SOLUTION                      STATUS

ALL             ▾              SELECT SOLUTION ▾             SELECT STATUS ▾

FACILITY                       PRIORITY                      SORT

SELECT FACILITY ▾              SELECT PRIORITY ▾             ORDER BY        ▾

CLEAR ALL    APPLY

☒ EXTRACT ISSUE

ISSUES                                                       SEARCH ISSUE TITLE...    🔍

HNA USER APPLICATION NOT LAUNCHING                                                    #79
PRIORITY: 3-MEDIUM   STATUS: PENDING   SOLUTION: CORE SYSTEM
01 JUL 03:56                                                                          ✎

TEST ISSUE                                                                            #80
PRIORITY: 3-MEDIUM   STATUS: OPEN   SOLUTION: CORE SYSTEM
02 JUL 10:24                                                                          ✎

HNAUSER NOT LAUNCHING                                                                 #81
PRIORITY: 3-MEDIUM   STATUS: OPEN   SOLUTION: CORE SYSTEM
04 JUL 21:55                                                                          ✎

*FIG. 5.*

NEW ISSUE

GENERAL INFORMATION

STATUS *
OPEN

SUMMARY *
TITLE OF NEW ISSUE

CATEGORY *
SELECT CATEGORY

IMPACT *
SELECT IMPACT

RELATED EVENT
SELECT RELATEDEVENT

URGENCY *
SELECT URGENCY

DOMAIN
SELECT DOMAIN

DUE DATE

SOLUTION *
SELECT SOLUTION

PROVIDER CONTACT *
SELECT USER

CLIENT CONTACT
SELECT CLIENT CONTACT

☒ SET OWNERSHIP TO PROVIDER CONTACT

☐ I CERTIFY THAT I AM NOT UPLOADING AN IMAGE, OR ANY OTHER TYPE OF DOCUMENT, THAT CONTAINS PROTECTED HEALTH INFORMATION (PHI). I ACKNOWLEDGE LOCATION FOR PHI IS IN THE FIELD SPECIFIED FOR THIS SENSITIVE INFORMATION.

ATTACHMENT
BROWSE...

*FIG. 6.*

| MEDICAL CENTER:1-3H7XXBV:_CA HNA 2016 | | |
|---|---|---|
| ISSUES | | |
| BACK | | EDIT |
| GENERAL INFORMATION | | |
| STATUS | PENDING | |
| STATUS REASON | THIRD PARTY VENDOR ACTION | |
| IMPACT | 3-MODERATE/LIMITED | |
| URGENCY | 3-MEDIUM | |
| TITLE | HNA USER APPLICATION NOT LAUNCHING | |
| SOLUTION | CORE SYSTEMS | |
| CONTACTS | SANDEEP,AITHAL; PRATYUSH,KUMAR | |
| OWNER | 965 | |
| DOMAIN | | |
| DESCRIPTION | TEST | |
| RELATED EVENT | CONVERSION | |
| DUE DATE | | |
| LAST EDITED BY | SANDEEP.AITHAL@PROVIDER.COM | |
| ADDITIONAL DETAILS | | |

*FIG. 7.*

ADOPT

[← BACK]

ADOPT TEST - DO NOT TEST RESOLVE | COUNTY HOSPITAL AUTHORITY | 2019-06-29

[NEEDS ATTENTION ②]   [ACKNOWLEDGE ⓪]

[SEARCH]

SHOWING 1 TO 2 OF 2 ENTRIES                                    [PREVIOUS] [NEXT]

| PROVIDER NAME ↑↓ | KPI VALUE ↑↓ | POSITION NAME ↑↓ | KPI ↑↓ | ACTIONS |
|---|---|---|---|---|
| PROVIDER TEST, PHYSICIAN – HOSPITALIST CCL PROVIDER | 0 | PHYSICIAN – HOSPITALIST | CPOE% | ☒ ☑ ⊞ |
| PROVIDER TEST, PHYSICIAN – HOSPITALIST PROVIDER | 100 | PHYSICIAN – HOSPITALIST | CPOE% | ☒ ☑ ⊞ |

SHOWING 1 TO 2 OF 2 ENTRIES                                    [PREVIOUS] [NEXT]

*FIG. 8.*

- EVENTS
- CLIENTS
- RESOURCES
- ROLES
- PROJECTS
- CONFIG ADMIN

EDIT EVENT CLIENT SCHEDULE PROJECT NOTIFY CONFIG-
EVENT RESOURCES CONTACT RESOURCES DETAILS RESOURCES ADOPT
CONVERSION COACH USER | COMMAND CENTER USER

CLICK THE BUTTON TO FETCH COMMAND CENTER USERS FROM PPM

FETCH FROM PPM

EVENT RESOURCE – CONVERSION COACH USER

| ASSOCIATE ID ↕ | ROLE ↕ | EMAIL | SOLUTION ↕ | SOURCE ↕ | MSTEAMS GROUP MEMBERSHIP STATUS? | ACTIONS |
|---|---|---|---|---|---|---|
| TB050334 | TECHNOLOGY ARCHITECT | TYLER.BETTS@CO... | WOMEN'S HEALTH | PPM | ✖ | DELETE |
| KCO46095 | TECHNICAL ENGAGEMENT. | KEN.CANERON@C... | WOMEN'S HEALTH | PPM | ✖ | DELETE |
| HJ052126 | INTEGRATION ARCHITECT | HEMANT.JAISWAL... | ENGAGEMENT CONTROLLER | MANUAL | ✓ | |

| SCORE | INCIDENT ID | SOLUTION | SUMMARY |
|---|---|---|---|
| 13.770378 | 413062315 | | TEST SCRIPTS |

RESOLUTION
STATUS CLOSED
DESCRIPTION ARE THERE ANY TEST SCRIPTS THAT WE CAN USE TO TEST THE NEW ECQM'S?
WORK DETAILS  VIEW
ASSIGNEE SCHWARTZ, MARIE

| SCORE | INCIDENT ID | SOLUTION | SUMMARY |
|---|---|---|---|
| 13.767385 | 413062289 | | TEST SCRIPTS |
| 13.692663 | 1-6052473998 | | TEST SCRIPTS... |
| 13.2694845 | INC000014681461 | HEALTH ORGANIZATION MANG. | TEST SCRIPTS FOR ROI TESTING |
| 12.96363 | 405893798 | | PROBLEM MIGRATION TEST SCRIPTS |
| 12.852412 | INC000019223911 | SOARIAN SCHEDULING | V4.2.300 TEST SCRIPT |

SMART SEARCH
SEARCH SIMILAR HISTORICAL ISSUES  SELECTION SOLUTION
DID YOU FIND THE RESULTS HELPFUL?
SEARCH WITHIN RESULTS          PREVIOUS  NEXT
SHOWING 1 TO 10 OF 30 ENTRIES

| YOU HAVE ACKNOWLEDGED SUCESSFULLY. | X |

ADOPT

← BACK

ADOPT TEST- DO NOT TEST RESOLVE | COUNTY HOSPITAL AUTHORITY | 2019-06-29

| NEEDS ATTENTION ① | ACKNOWLEDGE ① |

| | ⊞ | ⊪ |
| PREVIOUS | NEXT |

SEARCH

SHOWING 1 TO 1 OF 1 ENTRIES

| PROVIDER NAME ↑↓ | KPI VALUE ↑↓ | POSITION NAME ↑↓ | KPI ↑↓ | ACTIONS |
|---|---|---|---|---|
| PROVIDER TEST, PHYSICIAN – HOSPITALIST CCL PROVIDER | 0 | PHYSICIAN – HOSPITALIST | CPOE% | ☒ ☑ ⊪ |

SHOWING 1 TO 1 OF 1 ENTRIES

| PREVIOUS | NEXT |

*FIG. 12.*

SYSTEM AND METHOD FOR CONVERSION ACHIEVEMENT

BACKGROUND

A conversion event is a significant milestone in the journey of a healthcare ecosystem. A conversion event is the period of time when a user first starts using a new healthcare IT platform (such as Cerner Corporation manufactured software). A conversion event can occur over the course of minutes, hours, days, or longer as the user becomes familiar with the new healthcare IT platform. The goal of any conversion event is for the user to adapt to the new healthcare IT platform efficiently.

During a conversion event, a user (such as a clinician) may have an issue with the new healthcare IT platform (a "platform issue"). Typically, the user must call a help line to resolve these platform issues. These typical methods are inefficient where some platform issues with the new healthcare IT platform are repeated from user to user, leading to redundancy and inefficiency. Further, the service who may answer the help line are random providing no continuity of service or prior knowledge about the user, leading to further redundancy and inefficiency. As described in more detail herein, aspects improve these technologies and conventional solutions.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In brief and at a high level, this disclosure describes, among other things, methods, systems, computer storage media, and graphical user interfaces for providing resources to a platform issue. An embodiment of the disclosure includes a system for modifying a platform schedule, including: a data store and a computing device; wherein the computing device: receives an indication during a conversion event to a new healthcare IT platform, via a first device at a healthcare facility, of a platform issue comprising a narrative of an issue with the new healthcare IT platform, receiving a plurality of event resources; receiving an indication of an event resource; associating the event resource with the platform issue; receiving a plurality of event data stores; determining a selection of the plurality of event dates associating the platform issue with a category of resolutions; determining an educational resource from the selection; and modifying the associated platform schedule to include the platform issue.

An embodiment includes non-transitory computer-storage media having computer executable instructions embodied thereon that when executed by a computer perform a method comprising: receiving via a first device at a healthcare facility an indication during a conversion event to a new healthcare IT platform of a platform issue; receiving a plurality of event resources; receiving an indication of an event resource from the plurality of event resources on a second device at a location separate from the healthcare facility; and associating the event resource with the platform issue; and modifying the associated platform schedule to include the platform issue.

Additional embodiments include a system for modifying a platform schedule, comprising: a computing device and a data store, wherein the computing device comprises an issue module to receive an indication of a platform issue, a collaboration module comprising a plurality of event resources, an interface module configured to receive an indication of event resources, and a modification component configured to modify the associated platform schedule to include the platform issue.

Additional examples of systems and methods to resolve platform issues are described below in the Detailed Description.

BRIEF DESCRIPTION OF THE DRAWINGS

Embodiments are described in detail below with reference to the attached drawing figures, wherein:

FIGS. 5-12 illustratively depict screen displays showing example graphical user interfaces for modifying a platform schedule to include a platform issue in accordance with embodiments of the present invention.

DETAILED DESCRIPTION OF THE INVENTION

Figure 1:
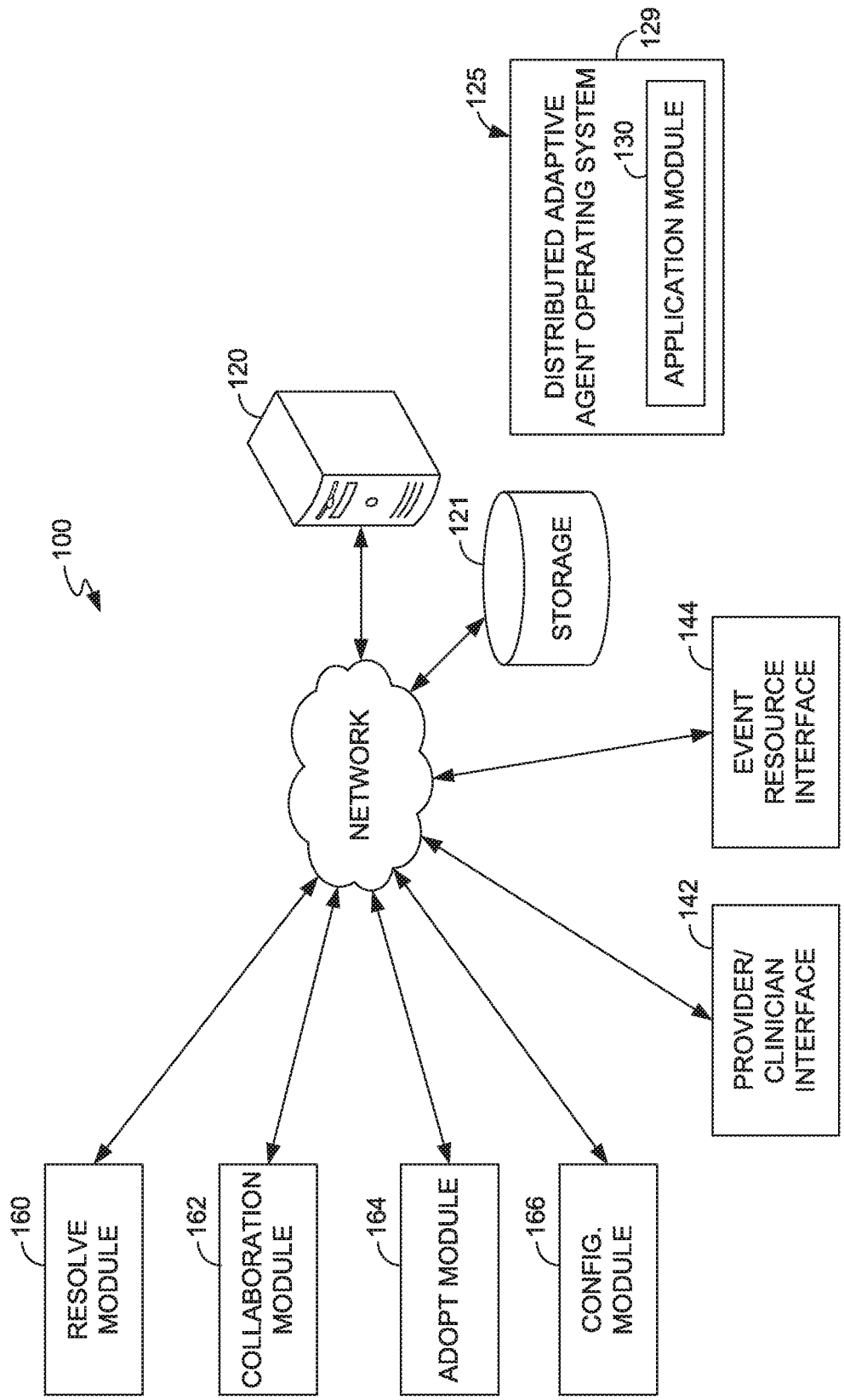
FIG. 1 illustrates is a schematic diagram of a suitable computing system environment for use in implementing the present invention in accordance with embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable nonremovable media, and contemplate media readable by a database, a switch, and various other network devices. By way of example, and not limitation, computer-readable media comprise media implemented in any method or technology for storing information, including computer-storage media and communications media. Examples of stored information include computeruseable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

Throughout this description, several terms are used to aid the understanding of certain concepts pertaining to the associated system and services. These terms intended to help provide an easy methodology of communicating the ideas expressed herein and are not necessarily meant to limit the scope of embodiments our technology. The following is a list of these terms: platform issue, an issue or problem a user may have while using a new healthcare IT platform; a user may be interchangeably referred to as a clinician or healthcare provider which includes any person tasked with interacting with the new healthcare IT platform (e.g., doctor, nurse, physician, etc.); a historical platform issue is a platform issue that occurred prior to the current platform issue, in some embodiments the historical platform issue may have been resolved or may in some embodiments may currently still be pending without resolution, in some embodiments the historical platform issue may include a narrative similar to that of the platform issues described herein; a healthcare IT platform is software service suite usable by a clinician to provide clinical services, including review of and modification to a patients electronic health record ("EHR").

Regarding the use of singular and plural, we do not mean to intend any sort of strict numerical implication by using the singular or plural of a term; similar to our lack of intent to imply the singular by using "a" or "the." Trying to capture the plural in words or in the FIGs. would often lead to wordiness. For example, though we might refer to "a database," clearly we fully anticipate that such reference would be equally applicable to multiple databases or more generally to data stores. By way of another example "a memory" does not imply one single memory device.

Historically, during a healthcare IT conversion event, IT personnel were located on site at a healthcare facility to help with training and educating clinicians on using the new healthcare IT platform during the conversion event. However, due to concerns about infectious disease spreading in a healthcare facility, the number of persons within a healthcare facility has been limited to patients and essential persons for providing medical care. To limit the number of personnel needed to be onsite during a conversion event, training and resources are used to assist a user. Users may have been using an older healthcare IT platform and have no familiarity with how to use the new healthcare IT platform. A user may have an issue such as how to access patient information and not know how to access that data in the new healthcare IT platform. The present disclosure enables the user, such as a clinician, to remotely generate an issue or question regarding the healthcare IT platform with a narrative of the problem to a central location, where a resolution can be managed in a central location without having to have in-person contact with IT personnel for training and educating. The present disclosure therefore overcomes the inefficiency of a user calling in to report an issue and IT personnel working face to face with the clinician regarding the issue or question. The present disclosure enables the user to briefly describe the problem from within the healthcare IT platform and the described systems and methods will allocate the platform issue to an event resource and/or educational resource to resolve the platform issue to a centralized system that is located remotely from the healthcare facility. The present disclosure does not require calling in or redundant work by the event resource. Other improvements over the prior art systems are apparent in view of the methods and systems described.

In brief and at a high level, this disclosure describes, among other things, methods, systems, computer storage media, and graphical user interfaces for modifying a platform schedule. The present disclosure improves prior art systems by automatically and efficiently assigning event resources to platform issues. By way of a high level example, systems and methods are provided for receiving an indication of a platform issue, which may be via a graphical user interface on a first device. The platform issue may include a narrative of an issue, explaining a problem the user has with a new healthcare IT platform. A plurality of event resources may be received. The plurality of event resources may include IT platform trainers and/or consultants designated to resolve platform issues with the new IT platform, as described herein. Each of the event resources may include an associated platform schedule. The platform schedule may be a plurality of platform issues assigned to the event resource, for example, a docket of platform issues to be resolved. An event resource of the plurality of event resources may be associated with the platform issue. The association may be an assignment of the event resource to resolve the platform issue. The association may be determined by a received indication of an event resource of a graphical user interface of a second device. The association may also be determined automatically based on the platform issue. An educational resource may also be determined based on the association of the event resource with the platform issue. In some embodiments, the educational resource may be a resolution to a historical platform issue. The associated platform schedule may be modified to include the event resource and the educational resource. This modified platform schedule alerts the event resource of the event issue and the educational resource and can use the educational resource to resolve the platform issue for the user.

As illustrated in the high level summary above, the present disclosure assigns an event resource and/or educational resource to a platform issue, which is an improvement over the prior art systems. A user can submit a platform issue with a narrative of an issue. In some embodiments, the platform issue may be associated with an event resource based on the experience and/or skills of the event resource. In some embodiments, the platform issue may be associated with an event resource based on information about the user. Further, the present disclosure recites assigning an educational resource that may include a resolution to a historical platform issue. In some embodiments the educational resource may be determined or a selection may be received to associate the platform issue with the educational resource. Advantageously, a the event resource can be provided the educational resource or the user can be provided the educational resource to resolve the platform issue.

It is also of note that the present disclosure improves prior art systems by modifying a platform schedule. The present disclosure describes, as illustrated above, modifying a platform schedule to include the platform issue and/or educational resource. Previous systems had no way to receive platform issues and assign them to a platform. The present disclosure describes several aspects, including automatically modifying the platform schedule to include the platform issue to receiving an input on a graphical user interface to associate the platform schedule with the platform issue. Each of these embodiments improve prior art systems where previous systems failed to overcome the described inefficiencies and redundancies of the art.

Each of the improvements described above and more that are described herein, have the additional improvement of providing educational resources, modifying a platform schedule, and/or assigning an educational resource remotely from a healthcare facility. The number of persons in a healthcare facility can be limited to reduce spread of disease and infection. Each of the embodiments herein may enable remote assistance during a healthcare IT conversion event.

An exemplary operating environment suitable for use in implementing embodiments of the invention is described below.

Turning now to FIG. 1 there is presented an example operating environment 100 suitable for practicing embodiments of the invention. Example operating environment 100 includes a computerized system for compiling and/or running an embodiment of a method for modifying a platform schedule. In accordance with embodiments of the present invention. With reference to FIG. 1, one or more data sources such as the resolve module 160, collaboration module 162, adopt module 164, and configuration module 166 are communicatively coupled to network 175 which is communicatively coupled to computer system 120. In some embodiments, components of operating environment 100 that are shown as distinct components may be embodied as part of or within other components of environment 100. For example, the resolve module 160, collaboration module 162, adopt module 164, and configuration module 166 may be implemented in computer system 120. Similarly, one or more of the resolve module 160, collaboration module 162, adopt module 164, and configuration module 166 may perform functions for two or more of the other modules described in FIG. 1.

In embodiments, network 175 includes the Internet, and/or one or more public networks, private networks, other communications networks such as a cellular network, or similar network(s) for facilitating communication among devices connected through the network 175. Network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component shown communicatively coupled to network 175 and network 175. In such embodiments, the firewall may reside on a second component located between the first component and network 175, such as on a server, or reside on another component within network 175, or may reside on or as part of the first component.

Embodiments of the resolve module 160, collaboration module 162, adopt module 164, and configuration module 166 include one or more data stores of information described herein. Further, each of the modules described may further include one or more processor(s) for performing various functions described herein. In some embodiments, the resolve module 160, collaboration module 162, adopt module 164, and configuration module 166 may be implemented as a cloud-based platform or may be distributed across multiple physical locations.

Example operating environment 100 further includes provider clinician interface 142 communicatively coupled through network 175 to the resolve module 160, collaboration module 162, adopt module 164, and configuration module 166. Although environment 100 depicts a communicative coupling through network 175 between interface 142 and the resolve module 160, collaboration module 162, adopt module 164, and configuration module 166 it is contemplated that some embodiments of interface 142 may be directly communicatively coupled to the computer system 120. Embodiments of provider clinician interface 142 may take the form of a graphical user interface operated by a software application or set of applications on a client computing device such as a personal computer, laptop, smartphone, mobile computer, or tablet computing device. In one embodiment, the application includes a new healthcare IT platform manufactured by Cerner Corporation. In an embodiment, the application is a Web-based application or applet.

The provider clinician interface 142 may be a graphical user interface of the new healthcare IT platform where a user, such as a clinician, may submit a platform issue. Provider clinician interface 142 facilitates receiving an indication of a platform issue from a user. The provider clinician interface 142 may enable a user to interact with the new healthcare IT platform to receive, manipulate, and or view an EHR of a patient among various other usages of the healthcare platform. In some embodiments the user may interact with and submit the platform issue through the provider clinician interface 142 of the healthcare IT platform. In some embodiments, interface 142 comprises a graphical user interface for receiving user input facilitating the receipt of the platform issue described in FIGS. 2-12.

Embodiments of provider clinician interface 142 may take the form of a user interface and application, which may be embodied as a software application operating on one or more mobile computing devices, tablets, smart-phones, front-end terminals in communication with one or more servers, back-end computing systems, laptops or other computing devices. In some embodiments, provider clinician interface 142 includes a Web-based application or set of applications that is usable to manage user services provided by embodiments of the invention.

Example operating environment 100 further includes event resource interface 144. Event resources may interact with various embodiments of the described invention. In some embodiments, an event resource may interact with, receive, and/or assign educational resources and/or platform issues to modify a platform schedule. The event resource may submit the platform issue via the event resource interface 144. In some embodiments, the event resource may interact with and/or submit the described commands via event resource interface 144. In some embodiments, interface 144 comprises a graphical user interface for receiving input facilitating the modification of the associated platform schedule as described in FIGS. 2-12.

The event resource interface 144 may be a graphical user interface remote from the new healthcare IT platform where the event resource, may submit a platform issue, interact with the platform schedule or educational resource, and/or provider other platform services. Similar to the provider clinician interface 142, embodiments of event resource interface 144 may similarly receive a platform issue or present the modified associated platform schedule. The event resource interface 144 may take the form of a user interface and application, which may be embodied as a software application operating on one or more mobile computing devices, tablets, smart-phones, front-end terminals in communication with one or more servers, back-end computing systems, laptops or other computing devices. In some embodiments, event resource interface 144 includes a Web-based application or set of applications that is usable to manage user services provided by embodiments of the invention.

In some embodiments, the event resource interface 144 and provider clinician interface 142 may be presented on two different devices in communication over the network 175. For example, the event resource interface 144 may be at a second device at a location separate from a healthcare facility and the provider clinician interface 142 may be at a first device at the healthcare facility. Providing the two interfaces 142 and 144 at different devices may enable an event resource to better service a user without being near or at the same device, further enabling remote services.

Example operating environment 100 further includes computer system 120, which may take the form of a server, and which is communicatively coupled through network 175 to the event resource interface 144, provider clinician interface 142, the resolve module 160, collaboration module 162, adopt module 164, and configuration module 166.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

In some embodiments, computer system 120 is a computing system made up of one or more computing devices. In some embodiments, computer system 120 includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Embodiments of computer system 120 include computer software stack 125, which in some embodiments operates in the cloud, as a distributed system on a virtualization layer within computer system 120.

The computer software stack 129 may be capable of hosting a number of services including the application module 130. The application module 130 may receive, modify, and submit data via the network 175 from each of the resolve module 160, collaboration module 162, adopt module 164, configuration module 166, provider clinician interface 142, event resource interface 144, and storage 121. In some embodiments, the application module 130 may perform the functions of the application layer described in FIG. 2. The application module 130 may receive the platform issue from one of the provider clinician interface 142 or event resource interface 144, and determine via at least one of the resolve module 160, collaboration module 162, adopt module 164, or configuration module 166 a platform schedule and modify the platform schedule with an educational resource and platform resource.

Figure 2:
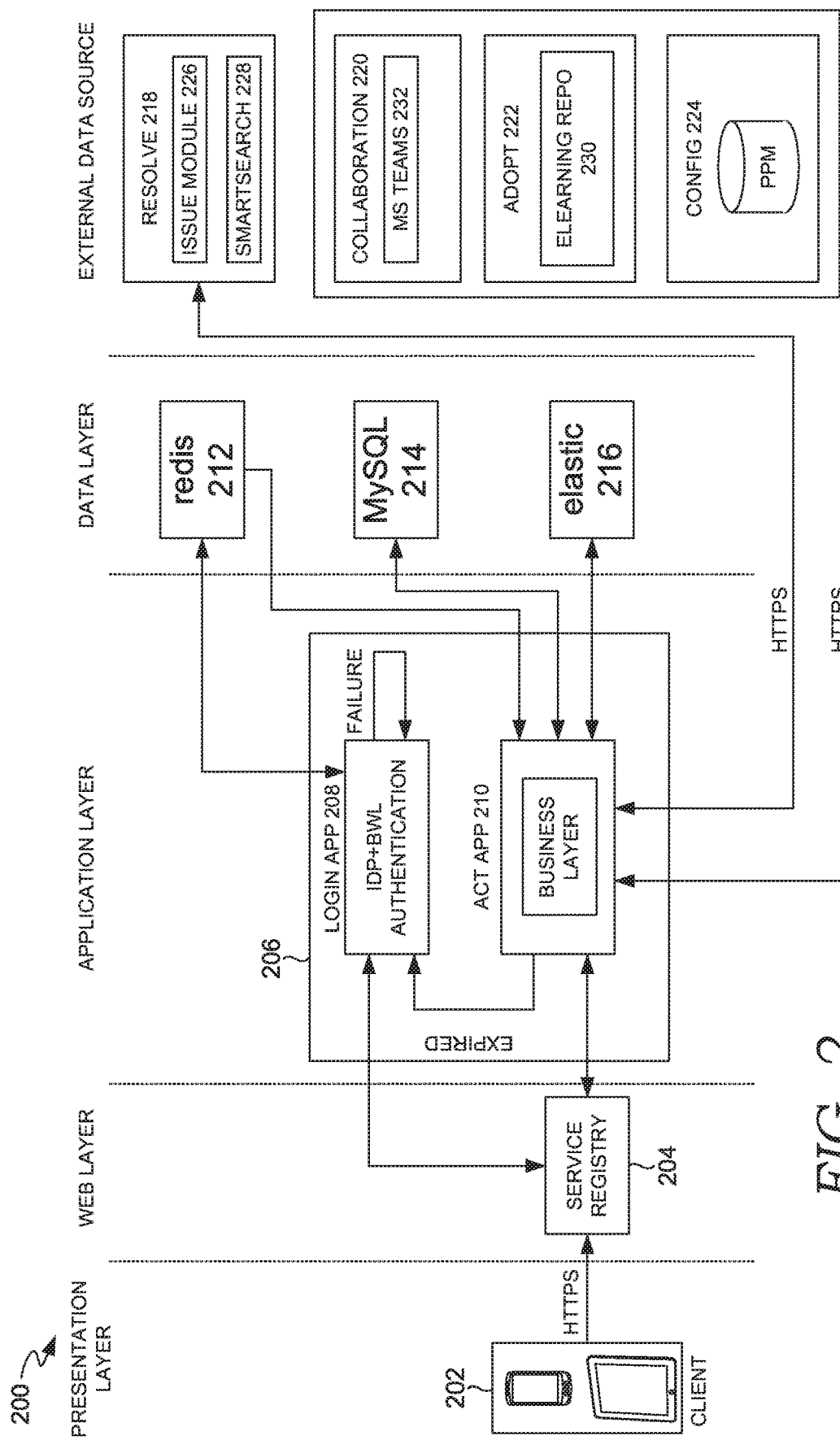
FIG. 2 depicts block diagrams of an exemplary system for facilitating modifying a platform schedule to a platform issue in accordance with embodiments of the present invention.

FIG. 2 depicts block diagrams of an exemplary system 200 for facilitating modifying a platform schedule to a platform issue in accordance with embodiments of the present invention. FIG. 2 illustrates the system 200 in a multitier architecture where each aspect of the presentation layer, web layer, application layer, data layer, and external data source where application processing and data management functions are physically separated. In some embodiments, the system 200 may be a single or a combination of tiers described herein, with the application processing and data management functions integrated at some layers. FIG. 2 illustrates the system 200 illustrates five layers, the presentation layer, the web layer, application layer, data layer, and external data source.

FIG. 2 includes the presentation layer with a client 202. The presentation layer may be the layer directly accessed by users and/or event resources described herein. The client 202 may be an embodiment of the event resource interface 144 and/or provider clinician interface 144. The client 202 includes one or more mobile computing devices, tablets, smart-phones, front-end terminals in communication with one or more servers, back-end computing systems, laptops or other computing devices. A user and/or event resource may interact with the client 202 to interact with the software and services described.

The client 202 may be in communication with service registry 204. Service registry 204 is illustrated on the web layer in communication with the application layer. The web layer illustrates the service registry may reside on the cloud described above, as a web based interface on the client 202. Service registry 204 communicates with the application layer to provide the application to the client 202. The service registry 204 may determine if the client 202 is logged in, or authorized to access the application. The service registry 204 may communicate the login application 208, and once authorization is confirmed, the service registry may provide the ACT application 210, described herein.

The application layer includes an application module 206. The application layer controls the application functionality by performing detailed processing. Application module 206 may determine and communicate various aspects of the described invention to the service registry 204. The application module includes login application 208 and ACT application 210. As described herein, the service registry 204 may provide the login application 208 to receive authorization before communicating the act application 210.

The login application 208 may authenticate a user and/or event resource from the client 202. The login application 208 may receive a request to authenticate from the service registry 204. The login application 208 may authenticate the event resource or user via credentials. The authentication in some embodiment may include an identity provider ("IDP") and/or BWL authentication. The authentication may include a user name, password, a one-time token, or other means of authentication. If the event resource and or user fails to authenticate the client 202 may be directed to submit new authentication identification. When the event resource successfully authenticates via the login app 208, the act application 210 may be communicated to the service registry 204.

The application module 206 further includes the act application 210. The act application 210 may communicate with the data layer and external data sources described herein to manage stored data. The application module 206 may store data from the external data sources via the data layer to provide the services, features, and functions described herein.

The data layer includes data persistence mechanisms which may be data servers, file shares, and others. The data layer encapsulates the persistence mechanisms and exposes the data. The data layer may provide an API to the application layer to expose methods of managing the stored data without exposing or creating dependencies on the data storage mechanisms. Avoiding the dependencies on the data layer may allow for updates or changes without the application tier clients being affected by or aware of the change. For example, the data layer, as illustrated may include redis data 212, my SQL data 214, and elastic data 216, which may be any data such as redis strings which may include JPEG images or serialized ruby objects. Each of the redis data 212, my SQL data 214 and elastic data 216 may include API to the application layer to manage stored data.

The data layer may implement a cache policy to improve performance of the act application 210. In some embodiments, the redis data 212 may be configured for more expensive data (e.g., with a longer time to retrieve) or static data elements (e.g., platform issues already submitted) of the stored data are cached. In some embodiments, the redis data 212 may be configured where the less expensive data (e.g., with a shorter time to retrieve) or active elements (e.g., platform issues open and/or being edited) of the stored data are cached. The cache policy may be tweaked based on specific platform events for the new healthcare IT platform. By implementing this cache policy, data that is both more expensive or less expensive can be more quickly accessed by the act application 210. In embodiments where the external data sources are in various methods of managing the stored data, the implementation of the cache policy allows for data to be managed across the various methods at increased speeds. For example, the cache policy may reduce the time to retrieve data than if the cache policy was not present.

Act application 210 may include a business layer, where the business layer may communicate with external data sources. The business layer may provide aspects of or access to each of the external data sources to the client 202. The business layer may facilitate the graphical user interfaces described in FIGS. 5-12. For example, the business layer may receive the platform issue from the provider clinician interface 142 and or the event resource interface 144 from storage in the data layer and/or storage 121.

The act application 210 is also in communication with the external data source. The act application 210 may communicate with the external data source over secure communication protocols. As illustrated, for example, the act application 210 may communicate with the external data source via Hypertext Transfer Protocol Secure (HTTPS).

The external data sources include a resolve module 218, collaboration module 220, adopt module 222, and configuration module 224. As illustrated, the external data sources may be external to the application layer and data layer. The external data sources may not exclusively refer to data, but also to functions and software integrations (such as third party integrations). Each external data source may be independent from each other at different locations, devices, and/or servers. In some embodiments, each of the modules described in the external data source layer may be correlated with each other. For example, as illustrated, the resolve module 218 may be separate from the combination of the collaboration module 220, adopt module 222, and configuration module 224.

The business layer may implement aspects of the data layer in order to organize, modify, and receive data from the external data sources. In some embodiments the external data sources may each require different aspects of the data layer. For example, the resolve module 218 may require the API of the redis data 212.

The resolve module 218 includes the issue module 226 and the smart search module 228. The resolve module 218 enables platform issues to be logged and resolved quickly. The resolve module 218 includes issue module 226, which may be used to receive an indication of a platform issue, for example, from provider/clinician interface 142 and/or event resource interface 144, described in FIG. 1. Stated differently, platform issues may be received from an event resource and/or a user.

The platform issue received by the issue module 226 may include a narrative of the platform issue. The narrative may include textual data such as a summary, description, resolution, work details, and the historical platform issue, image(s) (such as screenshots), and/or video(s) (such as screen capture). The platform issue may also or alternative include an identification of the user. The identification of the user may be automatic, based on authentication information received via the provider/clinician interface 142. For example, a user may login to the new healthcare IT platform and submit a platform issue. When the platform issue is submitted, contextual data such as who submitted the platform issue may be submitted with some or all of the information used for authentication. In some embodiments the platform issue may include the information about the user, such as an indication of the user. The indication of the user can be contact information, a name, email address, phone number and/or other identifier of the user.

The resolve module 218 may include features for issue allocation. Issue allocation enables routing of platform issues to relevant event resources. An event resource may include IT platform trainers and/or consultants designated to resolve platform issues with the new IT platform. Event resources may be coaches and experts in conversion of users to new healthcare IT platforms. For example, an event resource may be "Ben". Ben may be skilled at the new IT platform. When a clinician, Dr. Le, has an issue with the new IT platform, like how to add a new prescription to a patient, Dr. Le may submit a platform issue and Ben may be skilled to educate Dr. Le on how to add the new prescription to patients.

Each event resource may include a platform schedule. A platform schedule an assigned plurality of platform issues. A platform schedule may be a docket of assigned platform issues for an event resource. In some embodiments a single platform schedule may be assigned to multiple event resources, such as a pool of available event resources.

The configuration module 224 may store the platform schedule and event resource. The configuration module 224 may organize the platform schedule and event resources based on the platform issues associated with the platform schedules and event resources. This mapping may be used to automatically route resources with the issue module 226 without the issue module 226 organizing the data manually. Therefore, the act application 210 may modify an platform schedule and the configuration module 224 may receive the modification and store the modified data.

The configuration module 224 may fetch resources and other relevant information related to platform issues, educational resources, event resources, and platform schedules. In some embodiments the configuration module 224 fetches data to store the information centrally in the organized manner described above. Generated an organized mapping of the platform schedule and event resources described above is beneficial. Using spreadsheets based systems to organize platform issues and event resources which are unorganized and require additional computer resources to analyze.

The configuration module 224 further enables event resources to be notified centrally. In some embodiments, new educational resources may be developed and/or discovered. Via the configuration module 224, additional educational resources can be added and organized without manual notification of the event resource. The configuration module 224 can alert event resources to modifications to the data. In some embodiments, the notification may be submitted to a contact credential of the event resource, such as a phone number of email address.

Returning to the resolve module 218, the resolve module 218 may include features to enable automatic routing of platform issues to event resources. In some embodiments, the automatic routing of platform issues may be based on a solution tagged to the platform issue. For example, natural language processing may be used with a bank of terms (a solution tag) from the narrative linking the terms to an event resource with experience and/or skills in that area. For example, a narrative of the platform issue may include "I am unable to access patient EHR" the bank of terms may include "access" and the natural language processing may link that solution tag ("access") to an event resource who has previously dealt with access issues.

In some embodiments, the automatic routing of platform issues may include routing issues based on the identification of the user. As described herein, the indication of the user can be contact information, a name, email address, phone number and/or other identifier of the user. The resolve module 218 may receive the indication of the user with the platform issue. The resolve module 218 may include features to determine from a plurality of event resources which event resource has had the most interaction with the user based on the indication of the user. In some embodiments the resolve module 218 may determine the user based on the indication of the user such as cross referencing the received data with a data store of indications linked to users that were manually entered or from historical platform issues.

The resolve module 218 may also include features to enable manual routing ("associating") of platform issues to event resources. In some embodiments, the resolve module 218 may submit to the client 202 via the service registry 204 a graphical interface of a plurality of event resources. In some embodiments, the resolve module 218 may determine a selection of the plurality of event resources to display, by evaluating event resources that are more relevant to a particular issue potentially using aspects described above with regard to automatic routing of platform issues. An indication may be received of an event resource from the plurality of event resources, and the associated event resource may be associated with the platform issue and modify the event resource's corresponding platform schedule.

The resolve module 218 may include a smart search module 228. The smart search module 228 may enable identification of similar historical platform issues to the current platform issue faced by the user. Matching the historical platform issues to the current platform issue can be achieved by applying natural language processing techniques on an indexed data store of navigator and remedy tickets, to identify similar issues. In one embodiment, an API call is made to the application layer by passing a narrative of the platform issue, which processes those and returns similar historical platform issues to the application. A plurality of similar historical platform issues may be caused to be displayed on a graphical user interface, along with relevant educational resources on those results such as the narrative of a summary, description, resolution, work details, and the historical platform issue. The results can be filtered by specific solutions and indexed to provide more relevant results.

Referring briefly to the adopt module 222, the adopt module 222 may include an elearning repository 230. The elearning repository 230 includes educational resources. Via the act application 210, the resolve module 218 may receive information from the adopt module 222 such as from the elearning repository 230.

The elearning repository 230 may include educational resources. Educational resources may be a plurality of resolutions a platform issue where at least one of the plurality of resolutions are different. The educational resource may also or alternatively be a resolution to a historical platform issue, acting as a repository of resolved platform issues. In some embodiments the educational resource may be determined or a selection may be received to associate the platform issue with the educational resource. Advantageously, the event resource can be provided the educational resource or the user can be provided the educational resource to resolve the platform issue.

The resolve module 218 may receive the plurality of educational resources from the elearning repository 230. The resolve module 218 may determine automatically an educational resource of a plurality of educational resources based on a determination of a similar historical platform issue as described above. Historical platform issues may be stored in the elearning repository 230. The historical platform issues may include a resolution to the historical platform issue. The resolve module 218 may determine from the platform issue a matching educational resource or a set of educational resources based on a number of methods. For example, the resolve module 218 may implement natural language processing of the platform issue and/or the historical platform issues to find narratives between the two sets of data that are most similar statistically. In some other embodiments, the historical platform issues may include a set of key terms associated with the educational resource. The resolve module 218 may determine a keyword from the narrative of the platform issue such as by matching the keywords of the historical platform issues to the narrative of the platform issue. When multiple historical platform issues are determined to be similar to the platform issue, a set of historical platform issues or their affiliated educational resources may be submitted to a graphical user interface. Dissimilar platform issues may not be displayed. An event resource may select, and the resolve module receive an indication of the selection, of the educational resource most relevant to the platform issue.

Further, in some embodiments the narrative of the platform issue may not only be used to determine an educational resource. The platform issue generally and/or the event resource that was associated with the platform issue may be used to determine the educational resource. In some embodiments, the event resource associated with the platform issue may have previously resolved a history of platform issues. In some embodiments, only the history of platform issues resolved by the event resource may be implemented to determine the educational resource.

In some embodiments, an educational resource may be manually selected from a graphical user interface by an event resource. For example, the resolve module 218 may receive an indication of an educational resource. An event resource may manually search through the plurality of educational resources to resolve the platform issue.

Returning to the resolve module 218, the resolve module 218 may be implemented by the act application 210 to provide the various functions described herein. In some embodiments the act application 210 may communicate with the adopt module 222 to provide access to features such as the elearning repository 230.

The external data source further includes a collaboration module 220. The collaboration module 220 may provide a single enterprise collaboration platform for the user and the event resource to communicate. The collaboration module 220 may generate educational events for the user and event resource to resolve a platform issue. The collaboration module 220 may generate educational events via third parties. For example, and as illustrated, the collaboration module 220 may include a Microsoft teams feature 232. The collaboration module 232 may generate a chat between the user and the event resource via Microsoft teams feature 232. In some embodiments the educational event may be a meeting on the users calendar (such as Outlook) or another digital service such as Zoom.

In some embodiments, the collaboration module 220 generated educational events may be an event resource and be linked to the elearning repo 230. In these embodiments, the act application 210 may receive an educational resource via the methods described herein, and if the educational resource is determined to include an educational event, may communicate with the collaboration module 220 to generate a Microsoft teams meeting.

The external data source may further include the adopt module 222 with an elearning repo 230 (described above). The adopt module 222 may be used to track adoption metrics of each user. In previous systems of call centers, an event resource would not be provided any information about the training taken by the user of the new healthcare IT platform. The adopt module provides software and tracking of a user of modules of lessons learned about the new healthcare IT platform. This tracked information may be provided to the event resource via a graphical user interface automatically with the platform issue. Such information may be beneficial to an event resource as a platform issue of "how to access the EHR" may be resolved by recommending the user complete the uncompleted course in the users profile of "accessing patient EHR".

The resolve module 218 may modify the platform schedule stored in the configuration module 224. The resolve module modifies the platform schedule to include the platform issue and may include the educational resource. In some embodiments the modification of the platform schedule includes adding the user. The configuration module 224 may organize the platform schedule and event resources based on the platform issues. Modifying the platform schedule adds the platform issue and educational resource to assist the event resource in resolving the platform issue. A platform issue may be resolved efficiently with this modified platforms schedule.

Figure 3:
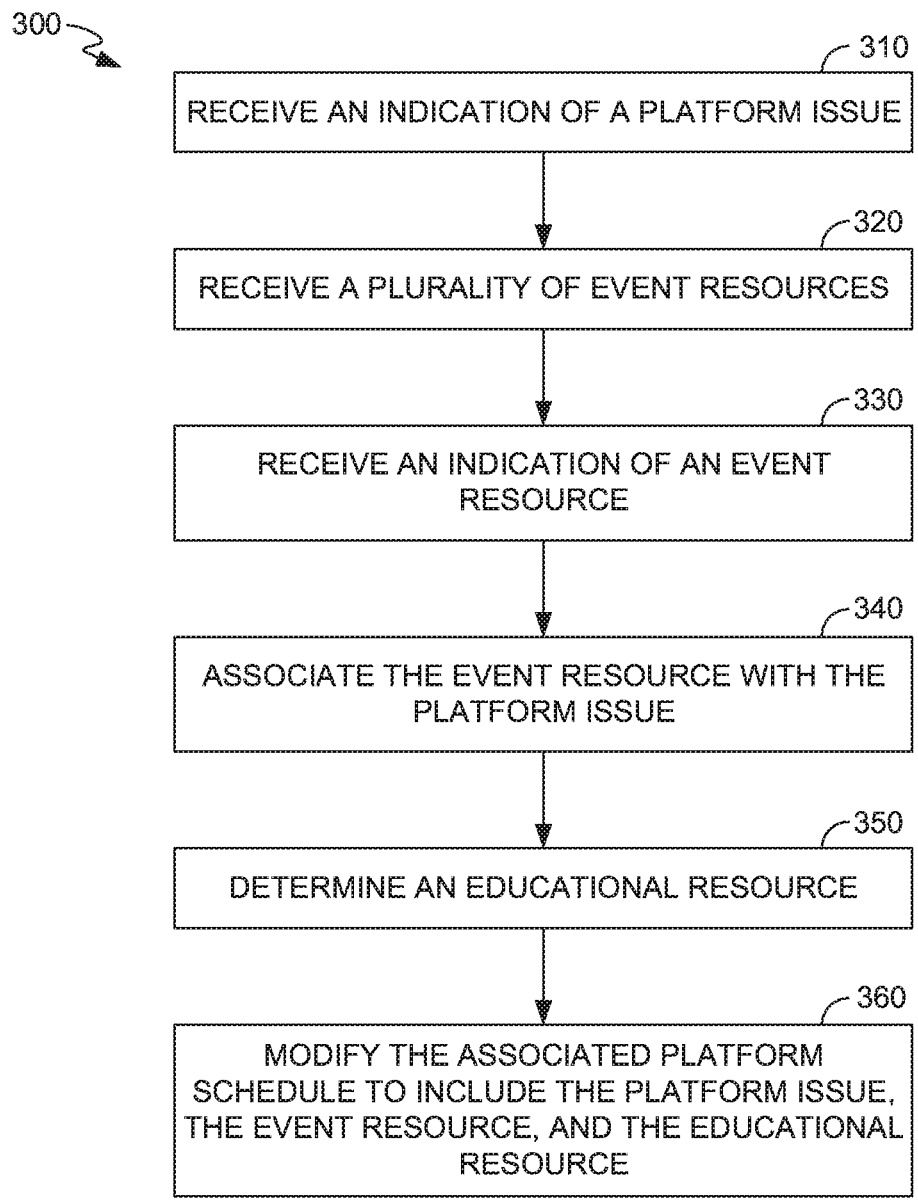
FIGS. 3-4 depict flow diagrams illustrating exemplary methods of modifying a platform schedule to include a platform issue in accordance with embodiments of the present invention.

FIG. 3 depicts a flow diagram illustrating an exemplary method 300 of modifying a platform schedule to include a platform issue. In some embodiments the method may be executed by one or more non-transitory computer-storage media having computer readable executable instructions embodied thereon.

Block 310 includes receiving an indication of a platform issue. The platform issue may be received by provider clinician interface 142, illustrated in FIG. 1. In some embodiments the exemplary method 300 includes receiving an indication during a conversion event to a new healthcare IT platform via a first device at a healthcare facility of a platform issue comprising a narrative of an issue with the new healthcare IT platform.

Block 320 includes receiving a plurality of event resources. The plurality of event resources may be stored in at least one data stores such as an external data source such as the configuration module 224, illustrated in FIG. 2. In some embodiments, the exemplary method 300 may include receiving a plurality of event resources wherein each event resource of the plurality of event resources comprises an associated platform schedule.

Block 330 includes receiving an indication of an event resource. The indication of the event resource may be received via event resource interface 144 of FIG. 1 and/or client 202 of FIG. 2. In some embodiments, the exemplary method 300 may include receiving an indication of an event resource of the plurality of event resources on a second device at a location separate from the healthcare facility.

Block 340 includes associating the event resource with the platform issue. The association of the event resource of a plurality of event resources may be determined by the resolve module 218, as described herein.

At block 350, the exemplary method 300 includes determining an educational resource. In some embodiments, determining the educational resource may be based on the association of the event resource with the platform issue. The educational resource may be stored in the adopt component 222 of FIG. 2 with a plurality of educational resources and the educational resource may be determined by the act application 210 in conjunction with the resolve module 218.

Block 360 includes modifying the associated platform schedule to include the platform issue, the event resource, and the educational resource. The platform schedule may be stored with and associated with each event resource of a plurality of event resources in the configuration module 224 of FIG. 2. In some embodiments, the exemplary method 300 includes modifying the associated platform schedule to include the platform issue, the event resource and the educational resource.

Figure 4:
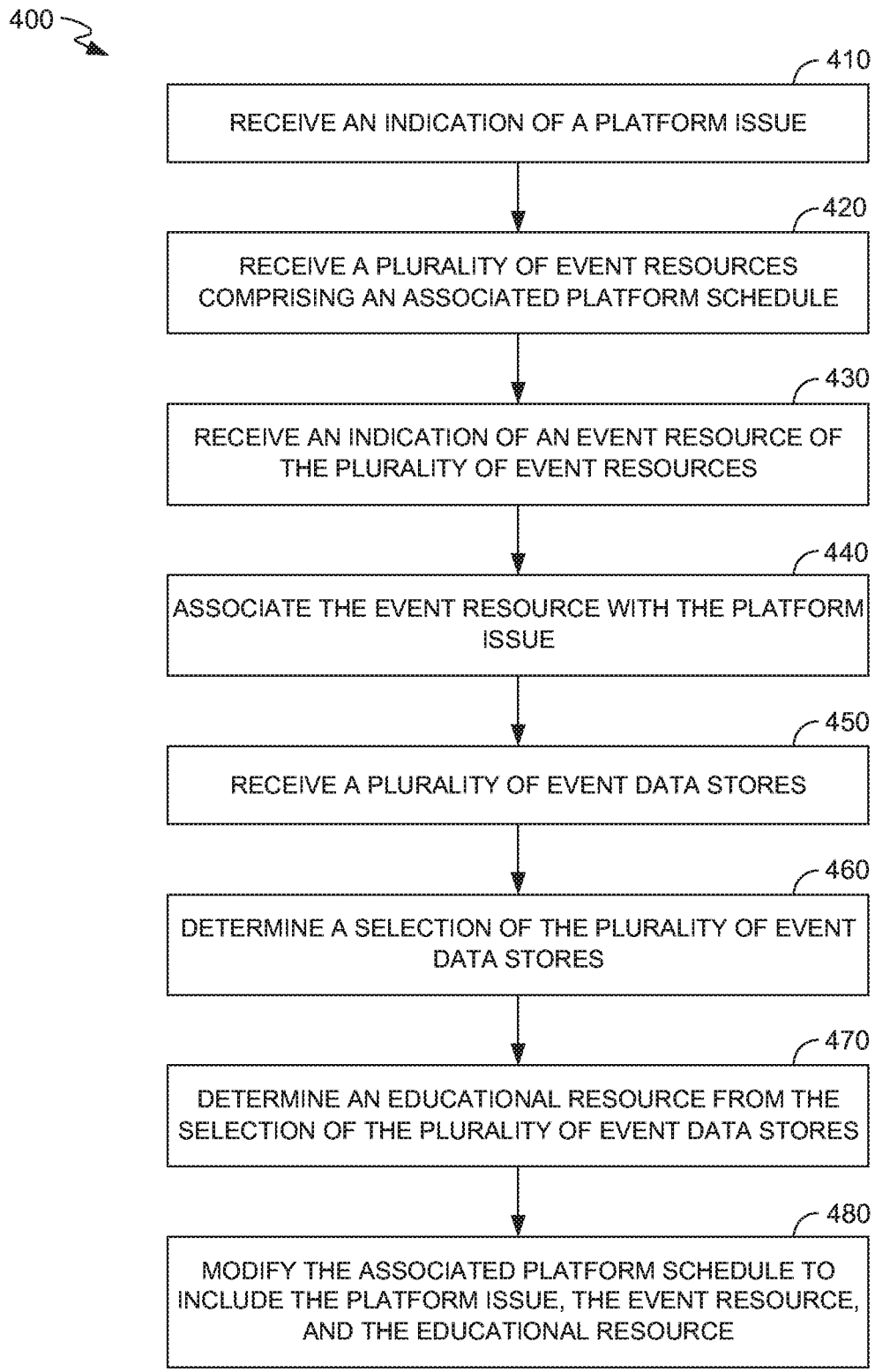

FIG. 4 depicts a flow diagram illustrating an exemplary method 400 of modifying a platform schedule to include a platform issue. In some embodiments the method may be executed by a system with a computing device having one or more processors and one or more computer-storage media and a data store in communication with the computing device. In some embodiments, the data store may be an external data source such as described in FIG. 2.

At block 410, the method includes receiving an indication of a platform issue. The platform issue may be received by provider clinician interface 142, illustrated in FIG. 1. The platform issue may include a narrative of an issue with an application. In some embodiments the exemplary method 400 may include receiving via a first device at a healthcare facility an indication during a conversion event to a new healthcare IT platform of a platform issue, comprising a narrative of an issue with the healthcare IT platform.

At block 420, the method includes receiving a plurality of event resources comprising an associated platform schedule. The platform schedule may be stored with and associated with each event resource of a plurality of event resources in the configuration module 224 of FIG. 2.

At block 430, the method includes receiving an indication of an event resource of the plurality of event resources. The indication of the event resource may be received via event resource interface 144 of FIG. 1 and/or client 202 of FIG. 2. In some embodiments the method may include receiving an indication of an event resource of the plurality of event resources on a second device at a location separate from the healthcare facility.

Block 440 includes associating the event resource with the platform issue. The association of the event resource of a plurality of event resources may be determined by the resolve module 218, as described herein.

Block 450 includes receiving a plurality of event data stores. In some embodiments, the exemplary method 400 includes receiving a plurality of event data stores comprising a plurality of educational resources, each of the plurality of educational resources comprising a plurality of resolutions to a plurality of historical platform issues, and each of the plurality of event data stores associated with a category of resolutions.

Block 460 includes determining a selection of the plurality of event data stores. The exemplary method 400 may include determining a selection of the plurality of event data stores associating the platform issue with the category of resolutions, the selection of the plurality of event data stores comprising a selection of educational resources. The selection of educational resources may be determined via the act application 210 and/or resolve module 218 of FIG. 2.

Block 470 includes determining an educational resource from the selection of the plurality of event data stores. In some embodiments, determining an education resource from the selection may be automatic or manually selected via an interface such as the event resource interface 144 of FIG. 1. The method at block 470 may include determining an educational resource from the selection of educational resources by a comparison of the platform issue to an associated historical platform issue of the plurality of historical platform issues of the selection of the plurality of event data stores.

At block 480 the exemplary method 400 include modifying the associated platform schedule to include the platform issue, the event resource, and the educational resource. For example, the exemplary method 400 may include modifying the associated platform schedule to include the platform issue, the event resource and the educational resource.

FIGS. 5-12 illustratively depict screen displays showing example graphical user interfaces for modifying a platform schedule to include a platform issue in accordance with embodiments of the present invention.

FIG. 5 illustrates an exemplary graphical interface illustrating how a platform issue may be submitted. FIG. 5 illustrates exemplary graphical displays of the provider clinician interface 142 or event resource interface 144, enabling a user or event resource to submit the platform issue. The illustrated FIG. 5 may be displayed on a first device at a healthcare facility as a provider clinician interface 142. The illustrated FIG. 5 may be displayed on a second device at a separate location from the healthcare facility as an event resource interface 144. Describing only embodiments of a user submitting a platform issue, a user or event resource may select "new issue" in FIG. 5 to log the platform issue. Simultaneously displayed in FIG. 5 is a list of issues. The list of issues, in embodiments where the graphical user interface is a provider clinician interface 142, may be a list of platform issues previously submitted for the particular user. In embodiments where the graphical user interface of FIG. 5 is an event resource interface 144, the list of issues may be the platform schedule for the particular event resource. The list of issues may indicate the status of the platform issue, such as pending, open, or closed (indicating the platform issue was resolved). The list of issues may further display the priority of each issue, a short summary of the platform issue, the date of the issue, and the educational resource for the platform issue.

FIG. 6 illustrates an exemplary graphical interface to an event resource, which may be displayed via the event resource interface 144 of FIG. 1. FIG. 6 illustrates some information that may be required and/or optional when submitted a platform issue. Required information in order to submit the platform issue is shown with a star, such as status of the platform issue, impact (which may be low, medium, high) solution, summary (which may be the title of the platform issue), provider contact, category, and urgency. Not required information may include domain, client contact, related event, due date, whether to set the ownership to the provider contact, attachments, and a certification of sensitive information.

FIG. 7 illustrates another exemplary graphical interface, illustrating a confirmation that the platform issue was recorded with an exemplary platform issue narrative. The confirmation of FIG. 7 illustrates, for the platform issue submitted the status as pending, status reason, impact, urgency, title, solution, contacts, owner, domain, description related event, due date, last edited by (which may be edited by the methods described herein, the event resource, or the user) and additional details.

FIG. 8 illustrates a graphical interface of a platform schedule for an event resource. The graphical interface may be displayed on the event resource interface 144. As described herein, the adopt module 218 may communicate with the configuration module 224 to display the platforms schedule for the event resource. Simultaneously displayed is a selection for the platforms schedule of items needing attention and acknowledged items. Displayed are the items needing attention of the platform schedule. At the bottom of the graphical interface is the platform schedule, which shows two items for the event resource. Each platform issue of the platform schedule includes the provider name, KPI value, position name, KPI, and actions. An event resource may take actions to resolve platform issues, such as email the user, edit the platform issue (such as add notes of the resolution and tasks performed) or see the educational resources (such as training) completed by the particular user. FIG. 12 illustrates the items acknowledged with similar features.

Figure 9:
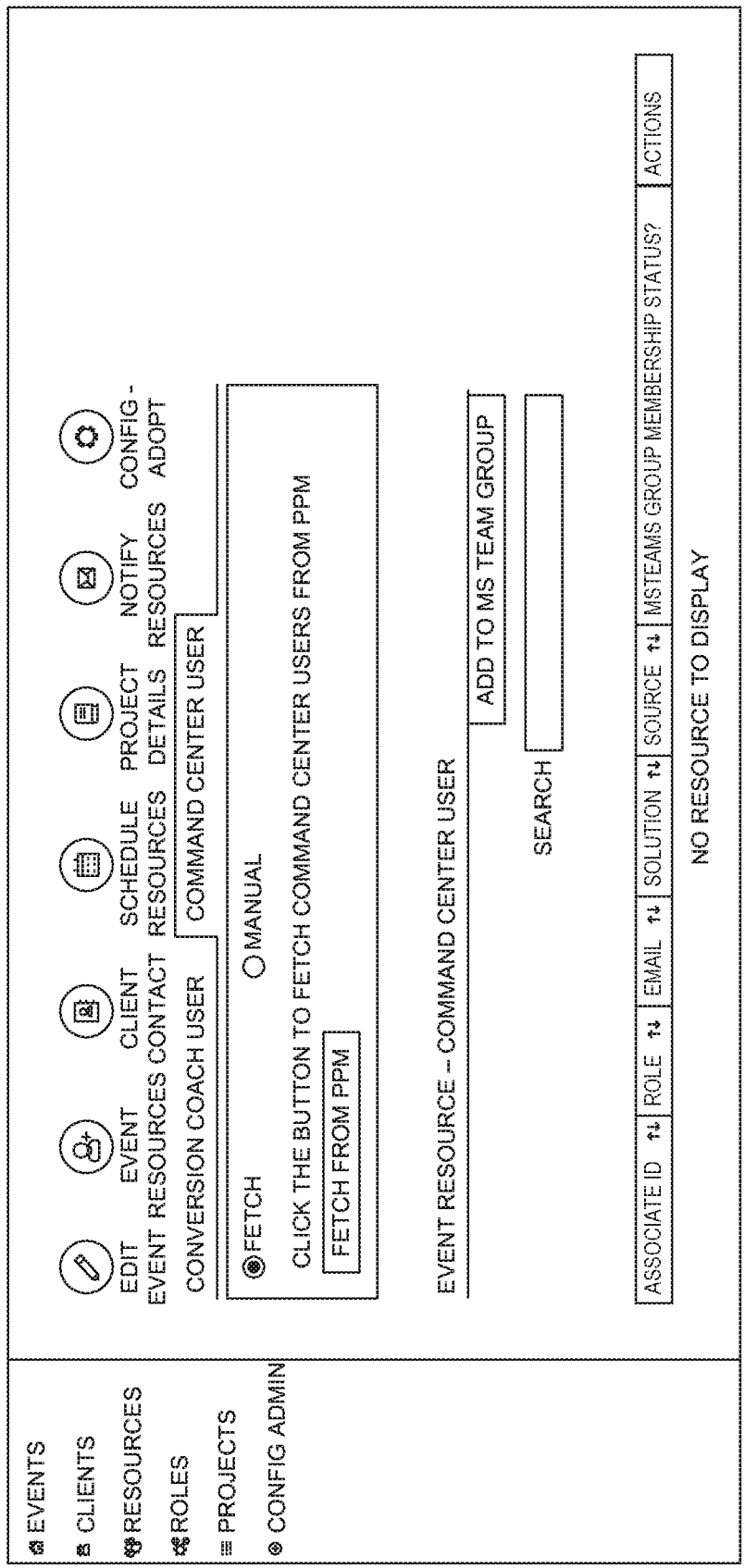

FIG. 9 illustrates a graphical interface of the collaboration module 220, which may assign an event resource by associate ID to resolve a platform issue via a MS teams group. The graphical interface may be displayed on the event resource interface 144. The event resource may edit the event, select additional or alternative event resources to resolve the platform issue, view client contact information, schedule resources such as a phone call or meeting, view project details (such as the platform issue details), may select to notify resources (such as contact the clinician that submitted the platform issue), or configure the platform issue. Simultaneously displayed is also the conversion coach user (described in FIG. 10) and command center user, with the option to fetch or manually retrieve command center users from PPM. Previously created MS teams groups may be shown in a list, as illustrated at the bottom of the graphical interface. Previously created MS teams groups may be organized and display associate ID, role, email, solution, source, and MS teams group membership status.

FIG. 10 illustrates another view of FIG. 9 but displaying the conversion coach user interface. The conversion coach user may click a button to fetch command center users. Simultaneously displayed are previous MS teams groups described in FIG. 9 with exemplary data as described in FIG. 9. Also displayed are the MS teams group membership status of "X" and a "checkmark" to illustrate a MS teams group has not been created or has been created, respectively.

FIG. 11 illustrates a graphical user interface with smart search features. The graphical interface may be displayed on the event resource interface 144. The interface enables searching for similar historical platform issues from a plurality of historical platform issues. A solution may also be selected for searching for educational resources. A voting system is also given where an event resource may describe if they found the results helpful. The event resource may provide in the search similar historical issues or the selection solution area search terms related to a platform issue. Related search terms may be displayed as shown below the search field. The related search terms may be implemented with a natural language processor to search for a specific platform issue or educational resource. The results of the search may be displayed with a field for the event resource to "search within results" to provide additional text. The results may include platform issues and/or educational resources and a summary of the platform issue or educational resource. For example in this graphical interface, the list of results may be organized by score (tied to whether results were helpful), incident ID, solution, and summary.

FIG. 12 illustrated another graphical interface of FIG. 8, illustrating the acknowledged field where a list of acknowledged platform issues may be listed. The graphical interface may be displayed on the event resource interface 144. Once the platform issue has been assigned an educational resource, the "acknowledged successfully" notice may be displayed to the event resource.

Additional embodiments of the present disclosure are contemplated that a person having ordinary skill in the art would recognize: One or more non-transitory computer-storage media having computer executable instructions embodied thereon that when executed by a computer perform a method of associating a platform issue from a first event resource to a second event resource, the method including: receiving an indication of a platform issue comprising a narrative of an issue with an application; receiving an indication of a first event resource to be associated with the platform issue, the first event resource associated with a first platform schedule; associating the first event resource with the platform issue based on the indication of the first event resource; receiving an indication of an educational resource comprising a platform resolution to the platform issue; modifying the associated first platform schedule to include the platform issue, the first event resource, and the educational resource; receiving an indication of a second event resource with a second platform schedule to be associated with the platform issue; associating the second event resource with the platform issue and disassociating the first event resource with the platform issue; and modifying the associated second platform schedule to include the platform issue, the second event resource, and the educational resource.

Additional embodiments include: One or more non-transitory computer-storage media having computer executable instructions embodied thereon that when executed by a computer perform a method of associating a platform issue from a first event resource to a second event resource, the method comprising: receiving an indication of a platform issue comprising a narrative of an issue with an application; receiving an indication of a first event resource to be associated with the platform issue, the first event resource associated with a first platform schedule; associating the first event resource with the platform issue based on the indication of the first event resource; receiving an indication of an educational resource comprising a platform resolution to the platform issue; modifying the associated first platform schedule to include the platform issue, the first event resource, and the educational resource; receiving an indication of a second event resource with a second platform schedule to be associated with the platform issue; associating the second event resource with the platform issue and disassociating the first event resource with the platform issue; and modifying the associated second platform schedule to include the platform issue, the second event resource, and the educational resource.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components are depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

What is claimed is:

1. One or more non-transitory computer-storage media having computer executable instructions embodied thereon that when executed by at least one computer of cause operations for modifying a platform schedule, the operations comprising:
   receiving by at least one processor a first indication that is associated with a conversion event of a healthcare facility to a new healthcare Information Technology (IT) platform and with a narrative of a platform issue with the new healthcare IT platform;
   receiving by the at least one processor a set of historical issues associated with a plurality of event resources, a set of historical narratives, and a set of educational resources, wherein each event resource is associated with a respective platform schedule that represents a docket of assigned platform issues;
   performing a first filtering operation based on the narrative to identify a subset of historical issues, of the set of historical issues, that are similar to the platform issue;
   performing a second filtering operation to identify an educational resource, of the set of educational resources, the second filtering operation comprising:
      based on the subset of historical issues, determining both:
         (a) a subset of educational resources, of the set of educational resources, associated with the subset of historical issues; and (b) an event resource associated with a resolution of the subset of historical issues;
causing presentation of the subset of educational resources on a second device that is associated with the event resource; and
receiving a second indication selecting the educational resource, from the subset of educational resources, from the second device; and
after receiving the second indication, associating the event resource with the platform issue and modifying a platform schedule associated with the event resource to address the platform issue with the educational resource.

2. The media of claim 1, wherein the subset of educational resources is determined from the set of educational resources based on the narrative and based on the event resource.

3. The media of claim 2, wherein the subset of educational resources comprises a subset of resolutions corresponding to each of a subset of narratives of historical platform issues; and
wherein determining the subset of educational resource is based on associating the platform issue with the subset of narratives.

4. The media of claim 1, wherein the platform schedule comprises an assigned plurality of platform issues for the event resource; and
wherein modifying the platform schedule comprises assigning the platform issue to the assigned plurality of platform issues.

5. The media of claim 1, wherein the educational resource is associated with an educational event that is generated based on the event resource and the platform issue.

6. The media of claim 1, wherein the platform issue is received from a data store; and wherein the operations further comprises:
modifying the data store to associate an indication of the event resource and the educational resource with the platform issue.

7. The media of claim 1, wherein each event resource of the plurality of event resources is associated with a contact credential; and wherein the operations further comprise:
causing presentation to the event resource of a notification of the platform issue and of at least one of the subset of the educational resource based on the associated contact credential.

8. The media of claim 1, wherein the modified platform schedule is configured to alert the event resource of the event issue and of the educational resource.

9. The media of claim 1, wherein the determination of the subset of educational resources is based further on a history of platform issues resolved by the event resource.

10. A system for modifying a platform schedule, the system comprising:
at least one computing device having one or more processors and one or more computer-storage media; and
a data store in communication with the at least one computing device, wherein the at least one computing device is configured to:
receive, via a first device at a healthcare facility during a conversion event of the healthcare facility to a new healthcare Information Technology (IT) platform, a first indication comprising a narrative of a platform issue with the new healthcare IT platform;
receive by the at least one processor a set of historical issues associated with a plurality of event resources, a set of historical narratives, and a set of educational resources, wherein each event resource is associated with a respective platform schedule that represents a docket of assigned platform issues;
perform a first filtering operation based on the narrative to identify a subset of historical issues, of the set of historical issues, that are similar to the platform issue;
perform a second filtering operation to identify an educational resource, of the set of educational resources, the second filtering operation comprising:
based on the subset of historical issues, determining both:
(a) a subset of educational resources, of the set of educational resources, associated with the subset of historical issues; and
(b) an event resource associated with a resolution of the subset of historical issues;
cause presentation of the subset of educational resources on a second device that is associated with the event resource; and
receive a second indication selecting the educational resource, from the subset of educational resources, from the second device; and
after receiving the second indication, associate the event resource with the platform issue and modify a platform schedule associated with the event resource to address the platform issue with the educational resource.

11. The system of claim 10, wherein the platform schedule comprises an assigned plurality of platform issues for the event resource; and
wherein the at least one computing device is further configured to modify the platform schedule by assigning the platform issue to the assigned plurality of platform issues.

12. The system of claim 11, wherein the at least one computing device is further configured to present a notification of the platform issue to the event resource on the second device based on a contact credential associated with the event resource stored at the at least one computing device.

13. The system of claim 11, wherein the plurality of educational resources are associated with a plurality of event data stores at an external computing device different than the at least one computing device.

14. The system of claim 10, wherein:
the first indication further comprises an indication of a user associated with the first device; and
the at least one computing device is further configured to present the educational resource to the user.

15. The media of claim 10, wherein the first indication further comprises an indication of a user associated with the first device; and wherein the at least one computing device is further configured to:
receive a plurality of platform courses completed for the user based on the indication of the user; and
modify the platform schedule to include the plurality of platform courses completed for the user.

16. A system for modifying a platform schedule, the system comprising:
at least one computing device having one or more processors and one or more computer-storage media; and
a data store in communication with the at least one computing device, wherein the at least one computing device comprises:
an issue module configured to receive, via a first device at a healthcare facility during a conversion event of the healthcare facility to a new healthcare Information Technology (IT) platform, a first indication comprising a narrative of a platform issue with the new healthcare IT platform;

a configuration module comprising information indicating a plurality of event resources associated with a respective plurality of platform schedules;

an interface module configured to communicate with a second device, wherein communicating with the second device includes at least receiving a second indication from the second device;

a resolve module comprising the issue module and configured to:

receive a set of historical platform issues associated with the plurality of event resources, a set of historical narratives, and a set of educational resources, wherein each event resource is associated with a respective platform schedule that represents a docket of assigned platform issues;

perform a first filtering operation based on the narrative to identify a subset of historical platform issues, of the set of historical platform issues that are similar to the platform issue; and perform a second filtering operation to identify an educational resource, of the set of educational resources, the second filtering operation comprising:

based on the subset of historical platform issues, determining both:

(a) a subset of educational resources, of the set of educational resources, associated with the subset of historical platform issues; and (b) an event resource associated with a resolution of the subset of historical platform issues;

causing presentation of the subset of educational resources on the second device via the interface module, wherein the second device is associated with the event resource; and receiving a second indication selecting the educational resource, from the subset of educational resources, from the second device via the interface module; and after receiving of the second indication, associate the event resource to the platform issue and modify a platform schedule associated with the event resource to address the platform issue with the educational resource.

17. The system of claim 16, wherein the first indication further comprises an indication of a user associated with the first device, and further comprising:

an adopt module, in communication with the issue module, comprising a plurality of platform courses completed for a plurality of users and configured to receive platform courses completed for the user based on the indication of the user;

wherein the resolve module is further configured to modify the associated platform schedule to include the platform courses completed for the user.

18. The system of claim 17, the adopt module further comprising a plurality of event data stores comprising a plurality of educational resources, each of the plurality of educational resources comprising a plurality of resolutions to a plurality of historical platform issues, and each of the plurality of event data stores associated with a category of resolutions.

19. The system of claim 18, wherein the resolve module is further configured to determine a first selection of the plurality of event data stores associating the platform issue with the category of resolutions, and wherein the first selection comprises a second selection of educational resources.

20. The system of claim 19, wherein the resolve module is further configured to determine an educational resource from the second selection based on a comparison of the platform issue to an associated historical platform issue.

* * * * *